United States Patent [19]
Daniel et al.

[11] Patent Number: 6,032,068
[45] Date of Patent: Feb. 29, 2000

[54] NON-INVASIVE MEASUREMENT OF FROZEN TISSUE TEMPERATURE USING MRI SIGNAL

[75] Inventors: Bruce L. Daniel, Palo Alto; Rosemary Kim Butts, San Francisco, both of Calif.

[73] Assignee: The Board of Trustees of the Leland Stanford Junior University, Palo Alto, Calif.

[21] Appl. No.: 09/026,023

[22] Filed: Feb. 19, 1998

[51] Int. Cl.$^7$ .................................................... A61B 5/055
[52] U.S. Cl. .......................................... 600/412; 324/315
[58] Field of Search .................................... 600/410, 411, 600/412; 324/315, 307, 309, 300, 312

[56] References Cited

U.S. PATENT DOCUMENTS

| | | | |
|---|---|---|---|
| 4,558,279 | 12/1985 | Ackerman et al. | 324/315 |
| 4,701,705 | 10/1987 | Rollwitz | 324/306 |
| 5,263,482 | 11/1993 | Leunbach | 128/653.2 |
| 5,378,987 | 1/1995 | Ishihara et al. | 324/315 |
| 5,433,717 | 7/1995 | Rubinsky et al. | 606/20 |
| 5,602,477 | 2/1997 | McCarthy et al. | 324/315 |
| 5,706,810 | 1/1998 | Rubinsky et al. | 128/653.1 |

OTHER PUBLICATIONS

Grant R. Pease, Ph.D., et al., "MR Image–Guided Control of Cryosurgery" JMRI 1995; 5:753–760.

Reiko Matsumoto, MD et al., "Monitoring of Laser and Freezing–induced Ablation in the Liver with T1–weighted MR Imaging$_1$," JMRI 1992; 2:555–562.

Wilson S. Wong, M.D., et al., "Cryosurgery as a Treatment for Prostate carcinoma", Cancer Mar. 1, 1997/ vol. 79/No. 5, pp. 963–974.

D. Longson, et al., "Use of MRI for Measuring Structures in Frozen Postmorten Brain", Brain Research Bulletin, vol. 38, No. 5, pp. 457–460, (1995).

J.C. Gilbert, et al., "MR Image Analysis for Assessing the Temperature Distribution in a Cryosurgical Frozen Region", Proceedings of International Society for Magnetic Resonance in Medicine Fourth Scientific Meeting and Exhibition, 1746 (1996).

Jen–Shin Hong, et al., "MR Imaging Assisted Temperature Calculations During Cryosurgery", Magnetic Resonance Imaging, vol. 12, No. 7, pp. 1021–1031 (1994).

*Primary Examiner*—Jeffrey F. Jastrzab
*Assistant Examiner*—Eleni Mantis Mercader
*Attorney, Agent, or Firm*—Townsend and Townsend and Crew LLP; Henry K. Woodward

[57] ABSTRACT

Temperature in frozen tissue can be measured from magnetic resonance signals from the frozen tissue based on spin-spin relaxation time (T2) or based on relative intensity of the magnetic resonance signals. Short echo times are required, and use of tailored RF pulses, non-Cartesian readouts, and multi-slice and 3D k-space acquisitions are preferably employed.

12 Claims, 2 Drawing Sheets

NON-INVASIVE MEASUREMENT OF FROZEN TISSUE TEMPERATURE USING MRI SIGNAL

This invention was made with Government support under contract T32CA09695 awarded by the National Institutes of Health. The Government has certain rights in this invention.

BACKGROUND OF THE INVENTION

This invention relates to the measurement of temperature of frozen tissue, and more particularly the invention relates to non-invasively measuring the temperature using Magnetic Resonance Imaging (MRI) signal measurements.

The measurement of temperature in frozen tissue is important in many fields including food science, cryobiology, and cryosurgery for example. In cryosurgery diseased tissue is treated by lowering the temperature of the diseased tissue. The monitoring of the temperature of the tissue is important so that normal tissue is not damaged while the diseased tissue is killed. The safety and efficacy of minimally invasive cryosurgery increased substantially with the use of ultrasound to monitor ice ball formation. However, recent studies of prostate cryosurgery indicate that to achieve high success in eradicating tumors, lesions must not only be frozen, but should be cooled to a lethal temperature of approximately −40° C. Because ultrasound cannot interrogate the interior of the ice ball, cryosurgeons have had to rely on invasive, percutaneously inserted thermocouples to monitor temperatures at a few selected points within the ice ball to monitor the freezing process.

Existing methods for monitoring of temperatures in frozen tissue includes probes, such as thermocouples, fiber optic sensors, or thermistors that are physically inserted or in contact with the tissue. During cryosurgery, this implies physically penetrating the target tissue with multiple thermal probes, resulting in a more invasive procedure. Furthermore, because MR imaging can provide a two- or three-dimensional map of temperature dependent signal changes, the distribution of temperatures in a frozen sample can be more accurately assessed.

Theoretical calculation of temperatures, based on heat transfer models have been used. Recently, it has been proposed that MR could be used to predict thermal gradients within tissues based on heat transfer models, and knowledge about probe temperature and tissue freezing properties. These methods are limited, however, because they merely infer the thermal gradient within the ice ball, rather than measure it directly. It is unclear how well they will perform in clinical cryosurgery where multiple probes are used, and where the freezing duty-cycles of various probes are continuously adjusted to control the shape of ice ball formation, and hence heat transfer in the ice ball is not at a steady state.

The use of MRI has been proposed for assisting in cryosurgery in the following references:

Pease, G. R. et al., MR Image-Guided Control of Cryosurgery. *JMRI* 5, 753–760 (1995).

Matsumoto, R. et al., Monitoring of Laser and Freezing-induced Ablation in the Liver with T1-weighted MR Imaging. *JMRI* 2, 555–562 (1992).

Gilbert, J. C., MR Analysis for Assessing the Temperature Distribution in a Cryosurgical Frozen Region. (Abstract) *Proceedings of International Society for Magnetic Resonance in Medicine Fourth Scientific Meeting and Exhibition* 3, 1746 (1996).

Hong, J S, MR Imaging Assisted Temperature Calculations During Cryosurgery. *MRI* 12, 1021–1031 (1994).

U.S. Pat. No. 5,433,717 discloses magnetic resonance imaging assisted cryosurgery employing T1 measurements to determine temperature distribution in unfrozen tissue regions.

The present invention is directed to measuring temperatures within the ice ball of frozen tissue during cryosurgery and provide non-invasive and more comprehensive monitoring of cryosurgery, in one illustrative application.

SUMMARY OF THE INVENTION

In accordance with one embodiment of the invention, spin-spin relaxation time, T2* (T2* is a T2 value compensated for system parameters) is mapped using magnetic resonance imaging techniques for frozen tissue. It has been discovered that a decrease in T2* for a frozen tissue correlates to a decrease in temperature. Accordingly, by determining T2* at locations within the frozen tissue, a corresponding temperature is established based on pre-established T2* versus temperature curves for the tissue.

Both signal intensity and T2* vary with temperature. Accordingly, short echo times (e.g. less than 1 ms) are required. Tailored RF pulses such as slice selective RF half pulses can be used to reduce echo delay.

Alternatively, MRI signal intensity can be used to establish temperature since signal intensity also varies with temperature. Again, short echo times are required.

Standard 2-D Fourier transform MR techniques also restrict the minimum TE by requiring phase-encoding gradients to be applied before acquiring the echo. Recently, nonCartesian readouts, which require no phase encoding gradients, and in which the effective echo time begins at the start of signal acquisition have been described, including spiral, twirl, and projection reconstruction. Further, multi-slice and 3-D k-space acquisitions can be used to allow temperature information to be gathered from throughout a three dimensional sample.

The invention and objects and features thereof will be more readily apparent from the following detailed description and appended claims.

DETAILED DESCRIPTION OF ILLUSTRATIVE EMBODIMENTS

Figures 1A, 1B:
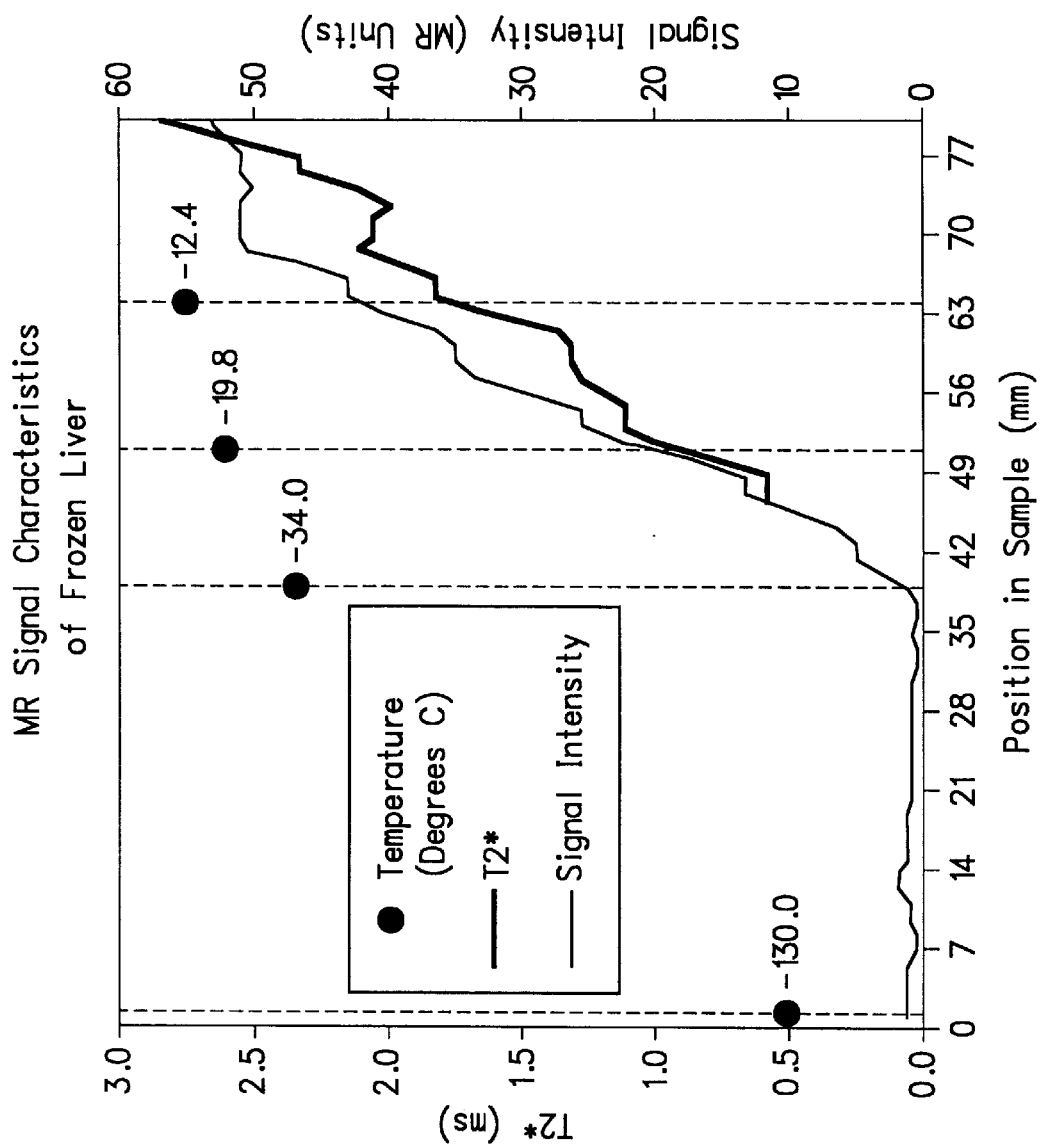
FIG. 1(a) is an image of two tubes of frozen liver.
FIG. 1(b) is a plot of signal intensity and T2* versus temperature for the liver samples.

FIG. 1(a) is an MR image of two tubes of frozen ex vivo liver, acquired at 1.5 Tesla and using echo TE of 1.2 ms. Temperatures in the left tube range from −12° C. at the bottom, where signal is highest, to −130° C. at the top, where there is no signal. The right tube is at a constant −12° C. and the signal is present throughout. FIG. 1(b) is a plot of signal intensity and T2* versus position in the left tube sample and temperature, illustrating that both T2* and signal intensity vary with temperature.

Figure 2:
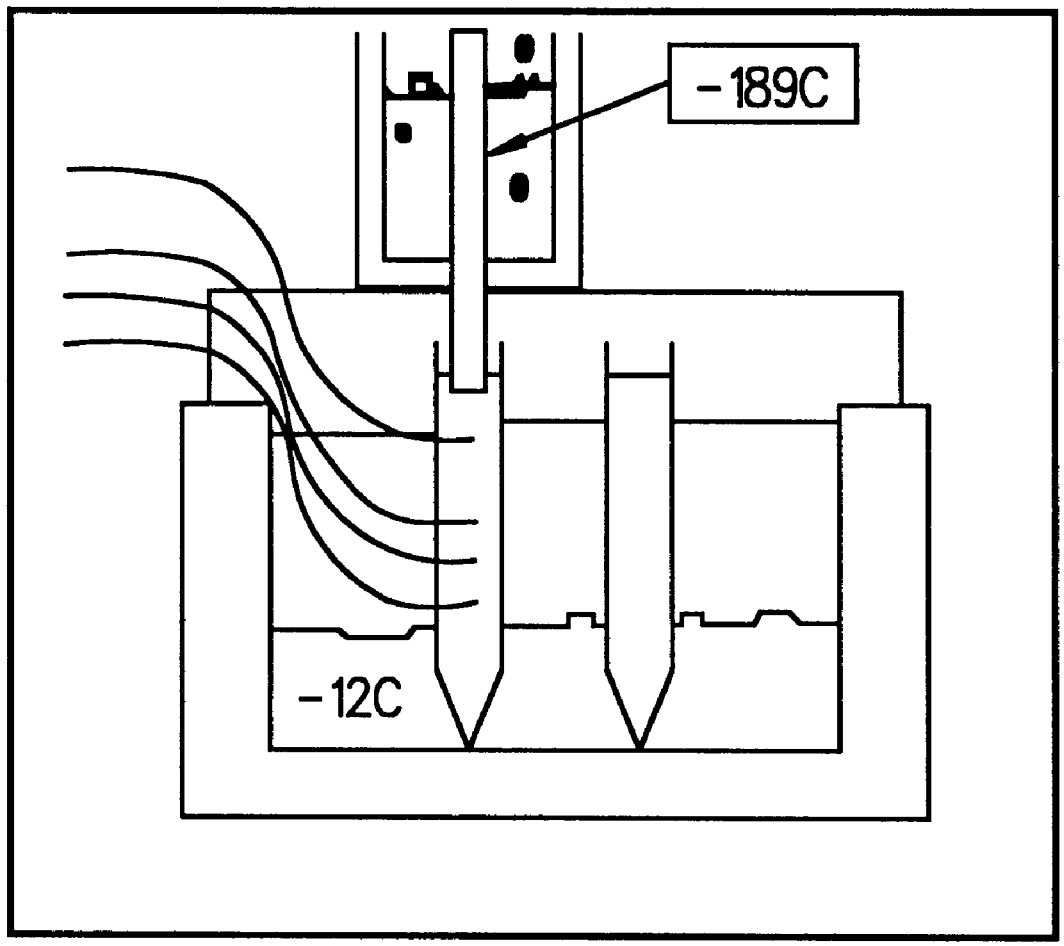
FIG. 2 illustrates apparatus for generating a steady state thermal gradient for the image of FIG. 1(a).

Imaging of a continuous range of sub-zero temperatures in the frozen ex-vivo bovine liver was performed using the apparatus in FIG. 2 as follows: Initially two 14 ml samples were prepared in plastic centrifuge tubes and were frozen in 12° C. freezer overnight. The bases of both samples were frozen within a 3 cm thick block of water in the bottom of a styrofoam container. This block of water functioned as a heat reservoir, so that the bases of both tubes remained near −12° C. throughout the experiment. Prior to freezing the specimens, an 8 mm diameter copper rod was inserted through the styrofoam lid of the container, so that it was in contact with the top surface of the liver tissue in the left tube. The other end of the rod traversed the bottom of an insulated plastic reservoir which was outside the styrofoam container. T-type thermocouples were inserted transversely into the sample at 4 locations via small holes drilled in the wall of the tube.

Prior to imaging the external reservoir was filled with liquid nitrogen, with a temperature of −189° C. The copper rod cooled the top of the liver sample in the top of the left hand tube by conduction. Temperature measurements at four thermocouples between the copper rod at the top of the sample and the −12° C. ice block heat reservoir at the base of the sample were repeated every few minutes until the thermal gradient within the sample stabilized. Imaging was then performed with short TE gradient echo technique. A pixel by pixel map of T2* was calculated by least squares fit of signal intensity on 4 gradient echo images with echo times of 1.2 ms to 2.4 ms.

MR imaging of thermal gradients during cryoablation of ex-vivo bovine (calf) liver specimen was performed using a prototype MR-compatible cryocatheter. This 2.9 mm diameter catheter cools to approximately −80° C. by means of the Joule-Thompson effect using high-pressure $N_2O$ gas fed from a cylinder safely outside the MR-scanner room. The cryocatheter casts a 6–7 mm diameter artifact on short-TE gradient echo imaging at 1.5T. Imaging of a 1 cm thick section of ex-vivo bovine (calf) liver immersed in room temperature water was repeated before, during, and after formation of an ice ball using the cryocatheter. Multiple spoiled gradient-echo images were performed using a conventional 1.5T whole body scanner (Signa Echosped, GE Medical Systems, Milwaukee, Wis.) with echo times ranging from 1.124 ms to 30.0 ms. T2* was calculated for regions of interest containing each sample by a monoexponential least squares fit of signal intensity as a function of echo time.

The tests were conducted with adipose and skeletal muscle as well as liver. While the relative signal intensities of adipose, liver and skeletal muscles for frozen and non-frozen tissues are substantially decreased compared with non-frozen tissues, they are adequate for imaging if very short echo times are used to compensate for rapid T2* decay. The signal from adipose tissue decreases the least due to freezing, followed by liver and skeletal muscle. No signal was detected from pure water ice below 0° C. The T2* and T1 for each tissue are given in Table 1. Note that T2* and T1 decreases for all frozen tissues. Unfortunately, T2* decay of adipose tissue at +6° C. could not be accurately calculated using echo times from 1.124 ms to 30.0 ms because the expected monoexponential T2* decay of signal intensity was modulated by the changing phase between the water and lipid components in the tissue.

Imaging of continuously distributed temperatures in frozen ex-vivo bovine liver confirms that signal intensity and T2* both decrease gradually with decreasing temperatures. The absence of significant signal in tissues frozen below about −25° C. precluded accurate measurement of T2* in this temperature range using the standard 2DFT short TE gradient echo imaging techniques available.

Imaging of the prototype cryoablation catheter revealed that signal intensity gradually decreased approaching the active cryoprobe using the short TE gradient echo technique. Such temperature-dependent MR signal characteristics were not observable in T1-weighted fast spin-echo images of the ice ball performed with echo times typically used for MR-monitoring of cryosurgery. Short-TE imaging obtained less than 2 minutes after turning off the cryoprobe revealed that although the overall ice ball size was unchanged, signal intensity no-longer decreased in the vicinity of the cryoprobe. As a result, susceptibility artifact from the probe became visible.

Ever since MR imaging was first proposed for monitoring cryosurgery, it has been assumed that frozen tissues have no perceptible MR signal. This assumption stems from the fact that the T2* of most crystalline solids is so short that it precludes conventional MR imaging. Indeed, pure water ice has no detectable MR signal. However, frozen tissues have sufficiently long T2* components that imaging is possible even when the tissues are frozen solid.

The explanation for the MR signal from frozen tissues is best understood by considering the gradual phase transition that occurs during slow freezing of biologic tissues, unlike the abrupt phase transition of liquid water. Freezing begins below about −1 degree C. when ice crystals nucleate, predominately in the vessels, and extracellular spaces of tissues. As freezing progresses, solutes are excluded from the growing ice crystal lattice, and remain within the diminishing volume of non-frozen tissue. Ice crystals continue to enlarge until the rising osmolarity of non-frozen tissues depresses the freezing point to the temperature of the tissue. Thus, even in a tissue which appears frozen solid, there is a liquid fraction of the water protons which remain excluded from the ice crystals. Usually, this fraction is quite small, because the volume of non-frozen tissue must decrease substantially before the solute concentration becomes high enough to significantly depress the freezing point. Nevertheless, we hypothesize that the liquid phase protons within this small fraction of hyperosmolar non-frozen tissue are the source of the MR signal.

As the temperature of the frozen tissue is lowered further, ice crystals continue to grow, consuming an ever increasing proportion of the mobile water protons. This process has been well documented in directional solidification models of the ice formation during cryosurgery, which reveal needles of ice occupying a greater fraction of the tissue in colder regions and a smaller fraction in less cold regions. Interestingly, MR signal intensity within frozen tissues also decreases with temperature, as shown in FIG. 1(b). Given that proton density is a major determinant of MR signal intensity, this result is consistent with the hypothesis that the MR signal within frozen tissues arises from the excluded liquid-phase protons.

The local environment of the excluded liquid-phase protons also alters their MR signal characteristics. Table 1 reveals that T1 adipose, liver and muscle shortened markedly with freezing. This may be due to the restricted mobility and decreased thermal motion of the super-cooled liquid phase protons which are trapped in the interstices between the ice crystals.

TABLE 1

| | Estimated T1/T2* | | | |
|---|---|---|---|---|
| | T2* | | T1 | |
| Tissue | +6 °C. | −16.6 °C. | +6 °C. | −16.6 °C. |
| Bovine Adipose | n/a | n/a | 332 ms | 32.3 ms |
| Bovine Liver | 11.5 ms | 1.23 ms | 357 ms | 43.7 ms |
| Bovine Muscle | 20.25 ms | 1.36 ms | 442 ms | 59.2 ms |

In Table 1, T1 and T2* were measured in ex vivo bovine adipose, liver and muscle tissues at +6° C. and −16.6° C. T1 was calculated by saturation recovery method from multiple gradient-recalled echo images obtained with TRs ranging from 20 ms to 2000 ms for tissues at +6° C., and with TRs ranging from 5 ms to 200 ms for tissues at −16.6° C. (Remaining Scan parameters: spoiled gradient recalled echo images, TE 1.124 ms, Flip Angle 90 degrees, Slice Thickness 2 cm; 2NEX.) T2* was calculated by monoexponential decay method from multiple gradient-recalled echo images obtained with TEs ranging from 1.124 ms to 30 ms for tissues at +6° C., and with TEs ranging from 1.124 ms to 3.2 ms for tissues at −16.6° C. (Remaining scan parameters: spoiled gradient recalled echo images, TR 100 ms, Flip Angle 30 degrees, Slice Thickness 2 cm; 8 NEX).

Freezing also reduced the T2* of liver and muscle tissue to less than 3 ms, as indicated in FIG. 1 and Table 1. This explains the lack of appreciable signal of standard imaging where echo times are usually at least several milliseconds. Furthermore, as noted in FIG. 1(b), T2* continues to decrease as the temperature of frozen liver falls. We hypothesize the shortening of T2* may be due to increases in local magnetic susceptibility caused by the ice crystals.

The ability of MR to image signal intensity and T2* variations that parallel the temperature of frozen tissues has significant implications for MR-monitoring of cryosurgery of cancer. In cryosurgery, the objective is not merely to freeze tissues, but to ablate them. Although cryosurgery in brain, skin, and prostate has been reported in a significant number of cases, tumor recurrences have precluded widespread acceptance of cryosurgery for cancer. For example, the rate of positive biopsies 2 years after prostate cryosurgery has been estimated at 15% to 83%. Recently the positive biopsy rate following prostate cryosurgery has been decreased to 10% by using invasive thermocouple monitoring which ensures that the prostate is not merely frozen, but cooled to a "lethal" temperature of −40° C.

Thermocouple temperature monitoring is limited because it is invasive, and temperature can only be monitored at a few points. Recently, it has been proposed that MR could be used to predict thermal gradients within tissues based on heat transfer models, and knowledge about probe temperatures and tissue freezing properties. These methods are limited, however, because they merely infer the thermal gradient within the ice ball, rather than measure it directly. It is unclear how well they will perform in clinical cryosurgery where multiple probes are used, and where the freezing duty-cycles of various probes are continuously adjusted to control the shape of ice ball formation, and hence heat transfer in the ice ball is not at a steady state.

The observation of temperature related MR signal variations raises the possibility of directly imaging the temperatures attained by cryosurgery. Short TE imaging can reveal signal changes corresponding to the thermal gradient present during cryosurgical ice ball formation, with lowest signal corresponding to the coldest temperatures in the immediate vicinity of the probe. Furthermore, soon after the cryoprobe is turned off, short TE MR images reveal that the temperature variations within the ice ball dissipate by thermal conduction, even though the overall ice ball size is unchanged.

Specialized MR imaging techniques have been developed that may provide imaging with even shorter echo times, including half k-space radio frequency excitation pulses, spiral imaging, and projection reconstruction. These will allow imaging of tissues with even shorter T2*, and hence may allow imaging of tissues below −35° C.

In summary, MR can be used to image frozen tissues as cold as −35° C., and the MR signal has a predictable dependence on tissue temperature. This ability to infer temperature in frozen tissues based on MR parameters has broad application in cryosurgery which has previously been limited by the lack of any non-invasive method to determine whether lethal temperatures have been achieved.

The invention has been described with reference to applicability in cryosurgery, but the invention has applicability in other fields also where non-invasive temperature measurement of frozen tissue is needed. Further, the described experiments are illustrative of the invention as other tissues and callibration curves could be used and measured. Thus while the invention has been described with reference to specific applications, experiments and embodiments, the description is illustrative of the invention and is not to be construed as limiting the invention. Various modifications and applications may occur to those skilled in the art without departing from the true spirit and scope of the invention as defined by the appended claims.

What is claimed is:

1. A method of measuring temperature in frozen tissue comprising the steps of:
    a) placing the frozen tissue in magnetic resonance imaging apparatus,
    b) obtaining magnetic resonance signals from the frozen tissue,
    c) determining spin-spin relaxation times within the frozen tissue, and,
    d) comparing the spin-spin relaxation times with known spin-spin relaxation times versus temperature of the frozen tissue to measure temperature.

2. The method as defined by claim 1 wherein step b) includes use of a short gradient echo technique.

3. The method as defined by claim 2 wherein step b) includes the use of slice-selective RF half pulses.

4. The method as defined by claim 2 wherein step b) includes the use of non-Cartesian readouts.

5. The method as defined by claim 2 wherein step b) includes use of multiplanar and 3D k-space imaging.

6. The method as defined by claim 1 wherein said method is part of cryosurgery.

7. A method of measuring temperature in frozen tissue comprising the steps of:
    a) placing the frozen tissue in magnetic resonance imaging apparatus,
    b) obtaining magnetic resonance signals from the frozen tissue,
    c) measuring signal intensity of the magnetic resonance signals, and
    d) comparing measured signal intensity with known signal intensity and attenuation characteristics versus temperature of the frozen tissue to measure temperature.

8. The method as defined in claim 7 wherein step b) includes use of a short gradient echo technique.

9. The method as defined by claim 8 wherein step b) includes the use of slice-selective RF half pulses.

10. The method as defined by claim 8 wherein step b) includes the use of non-Cartesian readouts.

11. The method as defined in claim 8 wherein step b) includes use of multiplanar and 3D k-space imaging.

12. The method as defined in claim 7 wherein said method is part of cryosurgery.

* * * * *